United States Patent
Czaplewski et al.

(10) Patent No.: US 9,921,207 B2
(45) Date of Patent: Mar. 20, 2018

(54) METHOD FOR DETERMINING WEAR OF A CONNECTOR CONTACT USING ATOM TRANSFER RADICAL POLYMERIZATION

(71) Applicant: International Business Machines Corporation, Armonk, NY (US)

(72) Inventors: Sarah K. Czaplewski, Rochester, MN (US); Joseph Kuczynski, North Port, FL (US); Jason T. Wertz, Pleasant Valley, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 191 days.

(21) Appl. No.: 14/923,967

(22) Filed: Oct. 27, 2015

(65) Prior Publication Data
US 2017/0115268 A1    Apr. 27, 2017

(51) Int. Cl.
| | |
|---|---|
| *G01N 31/10* | (2006.01) |
| *G01N 33/20* | (2006.01) |
| *G01N 33/44* | (2006.01) |
| *G01N 33/00* | (2006.01) |

(52) U.S. Cl.
CPC ........... *G01N 33/442* (2013.01); *G01N 33/20* (2013.01); *G01N 2033/0096* (2013.01)

(58) Field of Classification Search
CPC ........ G01N 31/10; G01N 33/20; C21C 21/06; C21C 21/12; C21C 21/10; C21C 21/16; C21C 1/026; C21C 21/14; C21C 21/18; H01R 13/03

USPC ...... 422/68.2; 436/2, 5, 6, 73; 526/111–122; 702/22, 23; 528/65–68

See application file for complete search history.

(56) References Cited

U.S. PATENT DOCUMENTS

| | | | | |
|---|---|---|---|---|
| 4,268,568 | A * | 5/1981 | Sard | H01H 1/60 174/110 FC |
| 5,077,563 | A * | 12/1991 | Takeuchi | B41J 2/3351 347/199 |
| 6,064,945 | A | 5/2000 | Gorenstein et al. | |
| 6,071,980 | A | 6/2000 | Guan et al. | |
| 6,274,254 | B1 * | 8/2001 | Abys | C25D 3/567 205/109 |

(Continued)

FOREIGN PATENT DOCUMENTS

| | | |
|---|---|---|
| WO | 9840415 | 9/1998 |
| WO | 2012067202 A1 | 5/2012 |
| WO | 2015166407 A1 | 11/2015 |

OTHER PUBLICATIONS

Antler, Morton; "Contact Fretting of Electronic Connectors"; IEICE Trans Electron; vol. E82-C; No. 1; Jan. 1999; pp. 3-12.

(Continued)

*Primary Examiner* — Brian J Sines
(74) *Attorney, Agent, or Firm* — Edward P. Li

(57) ABSTRACT

A method for examining wear of a connector contact using atom transfer radical polymerization. Metals in the connector contact are involved in atom transfer radical polymerization. In the method, polymers are formed via atom transfer radical polymerization. An average molecular weight and a polydispersity index of the polymers are determined. The exposure of underlying metal layers of the connector contact is determined based on the average molecular weight and atom transfer radical polymerization.

11 Claims, 3 Drawing Sheets

(56) References Cited

U.S. PATENT DOCUMENTS

| 8,101,711 | B2 | 1/2012 | Nelson et al. |
| 8,273,823 | B2 | 9/2012 | Matyjaszewski et al. |
| 8,404,788 | B2 | 3/2013 | Matyjaszewski et al. |
| 8,829,136 | B2 | 9/2014 | Glaser et al. |
| 8,975,346 | B2 | 3/2015 | Markanday et al. |
| 2014/0141647 | A1 | 5/2014 | Do |
| 2014/0350192 | A1 | 11/2014 | Alexander et al. |
| 2015/0132921 | A1 | 5/2015 | Park et al. |

OTHER PUBLICATIONS

Blanks, Henry; "Detection and Accelerated Testing of Vibration-Induced Connector Wear"; IEEE Transactions on Components, Hybrids, and Manufacturing Technology; vol. CHMT-7; No. 1; Mar. 1984; pp. 3-10; Copyright IEEE 1984.

Do, Trent et al.; "A Reliability Study of a New Nanocrystalline Nickel Alloy Barrier Layer for Electrical Contacts"; Amphenol TCS and Xtalic Corporation; Nashua, NH and Marlborough MA; Copyright IEEE 2010; pp. 1-9.

Guliashvili, Tamaz et al.; "Copper-Mediated Controlled/"Living" Radical Polymerization in Polar Solvents: Insights into Some Relevant Mechanistic Aspects"; Chem. Eur J.; 2012; vol. 18; www.chemeurj.org; Copyright 2012 Wiley-VCH Verlag GmbH & Co. KGaA, Weinheim; pp. 4607-4612.

U.S. Appl. No. 15/045,773, Entitled "Method for Determining Wear of a Connector Contact Using Atom Transfer Radical Polymerization", filed Feb. 17, 2016.

Appendix P.: List of IBM Patents or Patent Applications Treated as Related, Dated May 26, 2016, 2 pages.

\* cited by examiner

METHOD FOR DETERMINING WEAR OF A CONNECTOR CONTACT USING ATOM TRANSFER RADICAL POLYMERIZATION

TECHNICAL FIELD OF THE INVENTION

The present invention relates generally to determining wear of connector contacts, and more particularly to determining wear of connector contacts using atom transfer radical polymerization.

BACKGROUND

Wear of connector contacts is of great concern to the IT industry, due to the exposure of underlying layers of the connector contacts to environments that may cause corrosion. The exposure of the underlying layers is typically due to mechanical wear from excess plugging of connectors or can be associated with shock and vibe processes such as shipping.

Currently, when wear of a connector contact is examined, shock and vibe processes and plugging are first used to cause some wear of the connector contact. The connector contact typically comprises gold over nickel over copper. Once the test of shock and vibe or plugging is done, an evaluation of the wear of the connector contact must be done via an optical inspection. Then, the wear evaluation must be done via a scanning electron microscopy (SEM) examination. The above-mentioned method is the current process used for determining the exposure of the underlying metal networks in a connector contact. This method requires expensive equipment (more than US $250,000 currently) and is time consuming for examining many connector contacts.

SUMMARY

Embodiments of the present invention provide a method for examining wear of a connector contact using atom transfer radical polymerization. The method comprises placing the connector contact into a reactor and adding to the reactor chemicals for the atom transfer radical polymerization. The method further comprises determining an average molecular weight and a polydispersity index of polymers in a sample from the reactor. The method further comprises determining whether an underlying metal layer of the connector contact is exposed, based on the average molecular weight and the polydispersity index.

DETAILED DESCRIPTION

Embodiments of the present invention disclose a method for examining wear of a connector contact using atom transfer radical polymerization (ATRP). Metals in the connector contact are involved in ATRP. In the method, polymers are formed via ATRP. An average molecular weight and a polydispersity index (PDI) of the polymers are determined. The exposure of underlying metal layers of the connector contact is determined based on the average molecular weight and the PDI. The advantage of the method is that examining wear of connector contacts does not need a lengthy amount of time as used in an optical examination and a scanning electron microscope (SEM) examination. Additionally, the equipment for analyzing the PDI (e.g., permeation chromatography) is less expensive than the SEM equipment and it also does not require much maintenance.

Figure 1:
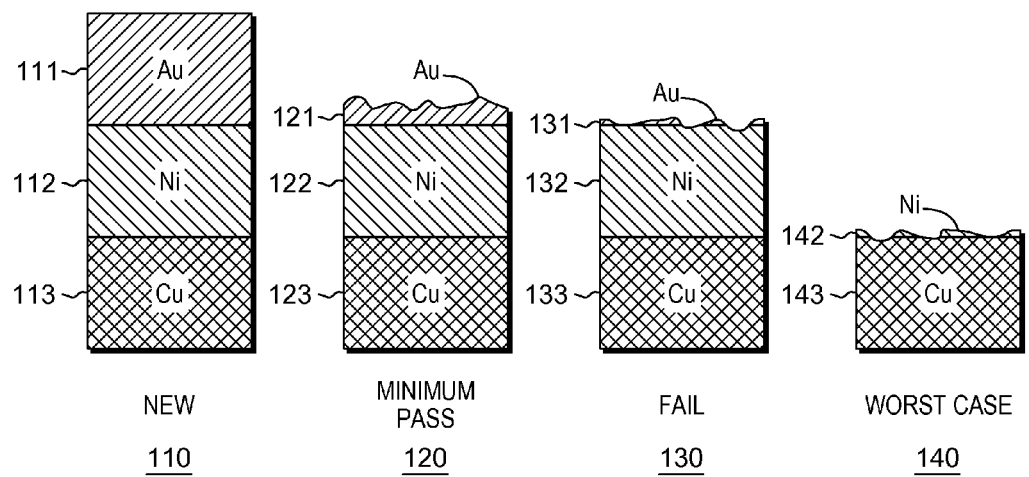
FIG. 1 shows diagrams illustrating metal layers of a connector contact under different conditions, in accordance with one embodiment of the present invention.

FIG. 1 shows diagrams 110, 120, 130, and 140 illustrating metal layers of a connector contact under different conditions, in accordance with one embodiment of the present invention. Diagram 110 shows metal layers of a new connector contact, which is before any mechanical wear from excess plugging or shock and vibe processes. As shown in diagram 110, the new connector contact comprises three metal layers: Au (gold) layer 111, Ni (nickel) layer 112, and Cu (copper) layer 113. Au layer 111 is the outermost metal layer of the connector contact, Ni layer 112 is an underlying metal layer and beneath Au layer 111, and Cu layer 113 is another underlying metal layer and beneath Ni layer 112.

Referring to FIG. 1, diagram 120 shows metal layers of a connector contact that passes the requirement for the minimum Au layer of the connector contact. The metal layers of the connector contact shown in diagram 120 include Au layer 121, Ni layer 122, and Cu layer 123. The thickness of Au layer 121, the outermost metal layer, is reduced after mechanical wear from excess plugging or shock and vibe processes; however, Au layer 121 still covers all surfaces of an underlying metal layer, Ni layer 122. Under Ni layer 122, there exists another underlying metal layer, Cu layer 123.

Referring to FIG. 1, diagram 130 shows metal layers of a connector contact that fails the requirement for the minimum Au layer of the connector contact. Au layer 131, the outermost metal layer, is mostly removed after mechanical wear from excess plugging or shock and vibe processes. Au layer 131 does not cover all surfaces of Ni layer 132; therefore, Ni layer 132 is exposed. Below Ni layer 132, there exists Cu layer 133.

Referring to FIG. 1, diagram 140 shows a worst case after mechanical wear from excess plugging or shock and vibe processes. In the worst case, an Au layer is completely removed. Ni layer 143 is mostly removed and does not cover all surfaces of Cu layer 143. Cu layer 143 is exposed.

Figure 2:
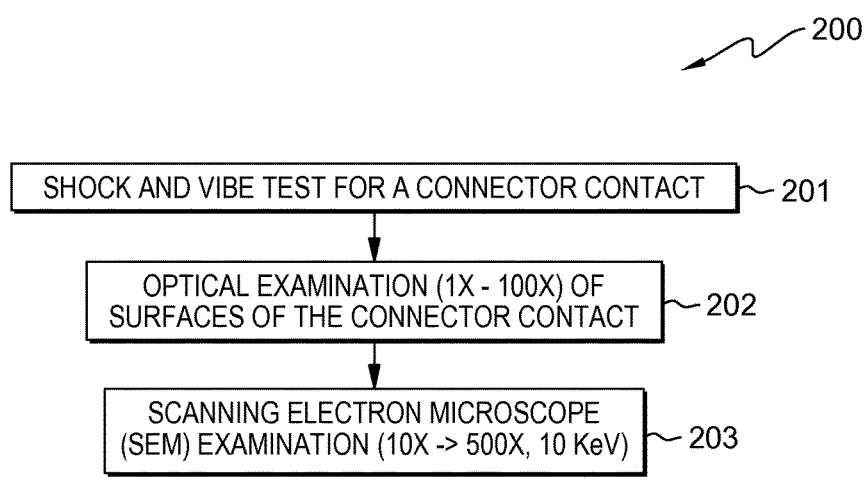
FIG. 2 shows a process of prior art for examining wear of a connector contact.

FIG. 2 shows process 200 of prior art for examining wear of a connector contact. Process 200 includes the following steps. At step 201, a shock and vibe test is conducted for the connector contact. At step 202, after the shock and vibe test, an optical examination of the surfaces of the connector contact is conducted. Usually, the magnification of the optical examination ranges from 1× to 100×. If there is evidence beyond light Au burnishing, at step 203, a scanning electron microscope (SEM) examination will be conducted. SEM produces images of the connector contact by scanning it with a focused beam of electrons. For example, the SEM examination is conducted with magnification of 10-500× at 10 keV. Secondary electron imaging (SEI) and back-scattered electron imaging (BEI) can be used to identify areas of potential excess wear including excess Au removal or exposed underplate metal layers and base metal layers. Energy-dispersive X-ray spectroscopy (EDS) is used to analyze the composition of the area identified by SEI or BEI.

Figure 3:
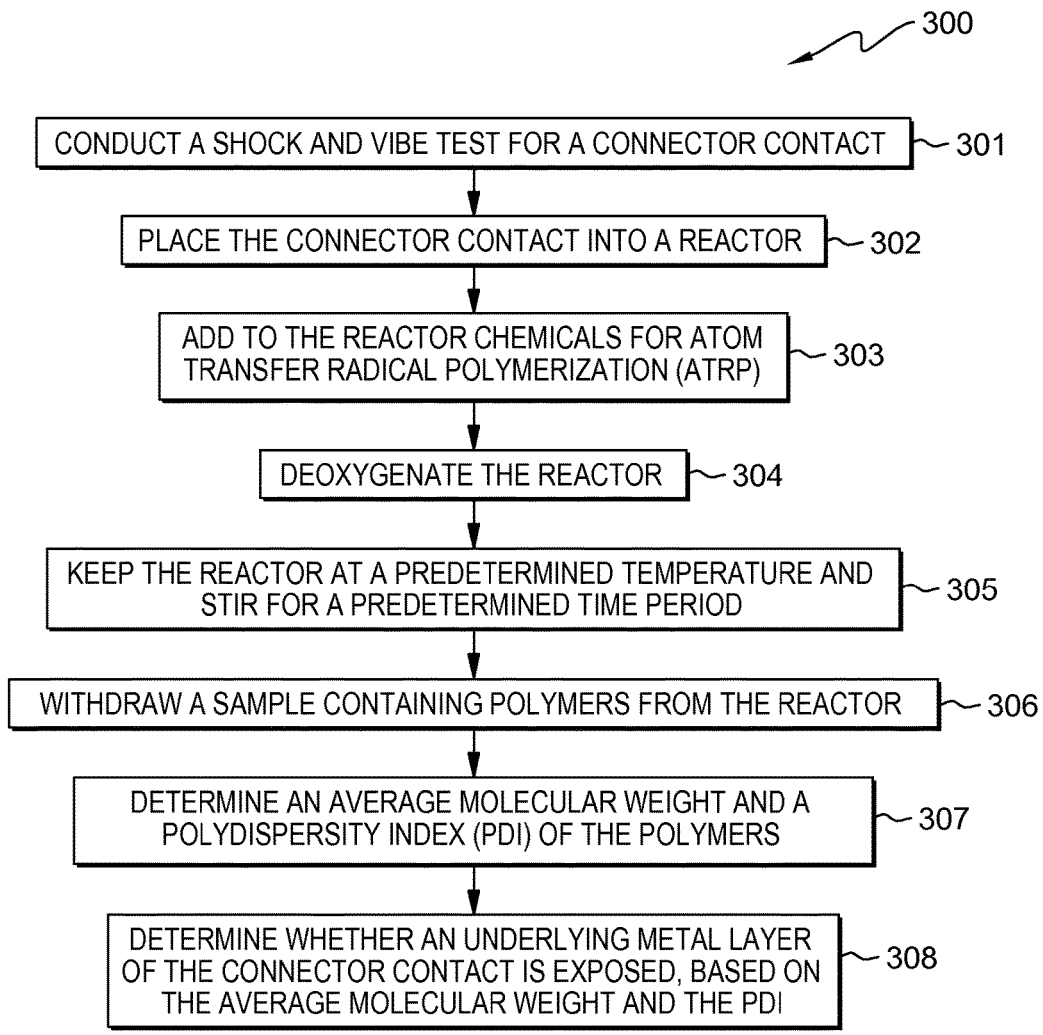
FIG. 3 shows a process for examining wear of a connector contact using atom transfer radical polymerization, in accordance with one embodiment of the present invention.

FIG. 3 shows process 300 for examining wear of a connector contact using atom transfer radical polymerization (ATRP), in accordance with one embodiment of the present invention. Process 300 for examining wear of a connector contact using ATRP includes the following steps. At step 301, a shock and vibe test is conducted for the connector contact. At step 302, the connector contact is placed into a reactor. For example, the connector contact is placed into a Schlenk reactor (or Schlenk flask) with a magnetic stir bar. At step 303, chemicals for the atom transfer radical polymerization (ATRP) are added to the reactor (for example, the Schlenk reactor or flask). In an embodiment, added chemicals include cupric bromide ($CuBr_2$), tris [2-(dimethylamino)ethyl]amine ($Me_6TREN$), dimethyl sulfoxide (DMSO), methyl acrylate monomer, and ethyl-2-bromopropionate (EBiB).

Atom transfer radical polymerization (ATRP) is a reversible deactivation radical polymerization. ATRP is a means of forming a carbon-carbon bond through a transition metal catalyst. ATRP uses a transition metal complex as the catalyst with an alkyl halide as the initiator (R—X). Transition metal complexes, such as complexes of Cu, Fe, Ru, Ni, and Os, can be used as catalysts for ATRP. In an ATRP process, the dormant species is activated by the transition metal complex to generate radicals using a one electron transfer process, and the transition metal is oxidized to a higher oxidation state. This reversible process rapidly establishes an equilibrium that is predominately shifted to the side with very low radical concentrations. The number of polymer chains is determined by the number of initiators. Each growing chain has the same probability to propagate with monomers to form living/dormant polymer chains ($R—P_n—X$). As a result, polymers with similar molecular weights and narrow molecular weight distribution can be formed. In ATRP, the catalyst is the most important component of ATRP because the catalyst determines the equilibrium constant between the active and dormant species. This equilibrium determines the polymerization rate. There are many different activator regeneration ATRP methods. The activator regeneration ATRP methods include initiators for continuous activator regeneration (ICAR) ATRP, activators regenerated by electron transfer (ARGET) ATRP, supplemental activator and reducing agent (SARA) ATRP, electrochemically mediated ATRP (eATRP), and photoinduced ATRP.

Referring to FIG. 3, at step 304, the reactor is deoxygenated. The deoxygenation may be through freeze-vacuum-thaw cycles and/or purge with nitrogen. At step 305, the reactor is kept at a predetermined temperature and stirred for a predetermined period of time. For example, the reactor is kept in a water bath at 25° C. and stirred for 30 minutes. Polymers are formed in the reactor through ATRP. At step 306, a sample of the polymers is withdrawn from the reactor. At step 307, an average molecular weight and a polydispersity index (PDI) of the polymers in the sample is analyzed. The PDI is a measure of the distribution of molecular mass in a given polymer sample, and it indicates the distribution of individual molecular masses in a batch of the polymers. The analysis of the PDI can be performed by many analytical methods. For example, the PDI can be analyzed by gel permeation chromatography (GPC). GPC is size exclusion chromatography and separates substances based on size. GPC is used to determine the relative molecular weight of the polymer samples as well as the distribution of molecular weights. Other methods for analyzing the PDI include light scattering measurement (such as dynamic light scattering) and direct measurement through spectrometry using matrix-assisted laser desorption/ionization and electrospray ionization mass spectrometry.

Referring to FIG. 3, at step 308, whether an underlying metal layer of the connector contact is exposed is determined, based on the average molecular weight and the PDI which are determined at step 307. If the nickel layer and the copper layer of a connector contact are not exposed (e.g., diagram 110 and 120 in FIG. 1), if atom transfer radical polymerization (ATRP) does not occur due to gold being a noble metal. If a value of the PDI is greater than 2, only the nickel layer is exposed (e.g., diagram 130 in FIG. 1); under this condition, a bimodal distribution is generated, which indicates that the polymerization is not a controlled living polymerization. If a value of the PDI is less than 2, the copper layer is exposed (e.g., diagram 140 in FIG. 1) and the reaction of the polymerization is favored. If there is presence of both Cu(0) and Ni(0), the bimodal curve leans more toward the copper reaction PDI due to the slow deactivation of the propagating radical in the Ni(0) reaction. The average molecular weight, the monomer conversion, and the PDI obtained over time are compared with standard profiles of the average molecular weight versus time, the monomer conversion versus time, and the PDI versus time for ATRP. Therefore, it can be determined which metal (Ni or Cu) initiates the polymerization reaction. Because only pinholes or small wear areas are exposed, the reactions may take a longer time, for example more than 30 minutes. In the process, it is not necessary for an operator to continuously check the reaction as the data will be matched back to the standard profiles based on the length of reaction time the operator chooses.

Based on the foregoing, a method has been disclosed for examining wear of a connector contact using atom transfer radical polymerization (ATRP). However, numerous modifications and substitutions can be made without deviating from the sprit and scope of the present invention. Therefore, the present invention has been disclosed by way of examples and not limitation.

What is claimed is:

1. A method for examining wear of a connector contact using atom transfer radical polymerization, the method comprising:
    placing the connector contact into a reactor;
    adding chemicals for the atom transfer radical polymerization to the reactor;
    determining an average molecular weight and a polydispersity index of polymers in a sample from the reactor; and
    determining whether an underlying metal layer of the connector contact is exposed, based on the average molecular weight and the polydispersity index.

2. The method of claim 1, further comprising:
    determining that no copper layer and no nickel layer are exposed, in response to determining that no atom transfer radical polymerization occurs.

3. The method of claim 1, further comprising:
    determining that a nickel layer of the connector contact is exposed, in response to determining that the polydispersity index is greater than 2.

4. The method of claim 1, further comprising:
    determining that a copper layer of the connector contact is exposed, in response to determining that the polydispersity index is less than 2.

5. The method of claim 1, further comprising:
    keeping the reactor at a predetermined temperature.

6. The method of claim 1, further comprising:
    stirring the reactor for a predetermined time period.

7. The method of claim 1, further comprising:
    withdrawing the sample containing the polymers from the reactor.

8. The method of claim 1, further comprising:
deoxygenating the reactor.

9. The method of claim 1, further comprising:
comparing the average molecular weight of the polymers with a standard profile of the average molecular weight versus time for the atom transfer radical polymerization; and
determining a metal that initiates the atom transfer radical polymerization.

10. The method of claim 1, further comprising:
comparing monomer conversion with a standard profile of the monomer conversion versus time for the atom transfer radical polymerization; and
determining a metal that initiates the atom transfer radical polymerization.

11. The method of claim 1, further comprising:
comparing the polydispersity index of the polymers with a standard profile of the polydispersity index versus time for the atom transfer radical polymerization; and
determining a metal that initiates the atom transfer radical polymerization.

\* \* \* \* \*